(12) United States Patent
Ferretti et al.

(10) Patent No.: US 7,723,292 B2
(45) Date of Patent: May 25, 2010

(54) COMPOSITIONS AND METHODS FOR TREATING CANCER

(75) Inventors: Fernando Ferretti, Bologna (IT); Anna Ferretti, Bologna (IT)

(73) Assignee: Fernando and Anna Foundation, Chicago, IL (US)

( * ) Notice: Subject to any disclaimer, the term of this patent is extended or adjusted under 35 U.S.C. 154(b) by 0 days.

(21) Appl. No.: 11/535,397

(22) Filed: Sep. 26, 2006

(65) Prior Publication Data

US 2008/0057052 A1 Mar. 6, 2008

(51) Int. Cl.
*A01N 37/18* (2006.01)
*A01N 61/00* (2006.01)
*A61K 38/00* (2006.01)
*A61K 31/00* (2006.01)

(52) U.S. Cl. ............................................. 514/2; 514/1
(58) Field of Classification Search ........................ None
See application file for complete search history.

(56) References Cited

U.S. PATENT DOCUMENTS

2004/0228860 A1* 11/2004 Taylor et al. ............. 424/144.1
2006/0002937 A1    1/2006 Schwaeble et al.

OTHER PUBLICATIONS

Son, Park, Chae, Moon, Lee, Song, Moon, Kang, Kwon, and Hong. Inhibitory effect of snake venom toxin from Vipera lebetina turanica on hormone-refractory human prostate cancer cell growth: induction of apoptosis through inactivation of nuclear factor kB. Molecular Cancer Therapeutics, 2007. vol. 6, pp. 675-683.*
Kim, D.S., Jang, Y., Jeon, O., and Kim, D. Saxatilin, a snake venom disintegrin, suppresses TNF-a-induced ovarian cancer cell invasion. Journal of Biochemistry and Molecular Biology, 2007. vol. 40, pp. 290-294.*
Vogel, C. and Muller-Eberhard, H.J. Induction of immune cytolysis: tumor-cell killing by complement is initiated by covalent complex of monoclonal antibody and stable C3/C5 convertase. Proceedings of the National Academy of Sciences, 1981. vol. 78, pp. 7707-7711.*
Huang, T.F., Yeh, C.H., and Wu, W.B. Viper venom components affecting angiogenesis. Haemostasis, 2001. vol. 31, pp. 192-206.*
Donato, N.J., Martin, C.A., Perez, M., Newman, R.A., Vidal, J.C., and Etcheverry, M. Regulation of epidermal growth factor receptor activity by crotoxin, a snake venom phospholipase A2 toxin. Biochemical Pharmacology, 1996. vol. 51, pp. 1535-1543.*
Didier Jean et al., "Co-expression and Secretion of C3, The Third Component of Complement and a C3-Cleaving Cysteine. Proteinase in a Highly Metastatic Human Melanoma Cell Line," Immunology Letters 58, pp. 107-112, 1997.
A. Kardosova et al., "Antioxidant activity of medicinal plant polysaccharides, " FITOTERAPIA 77, pp. 367-373, 2006.
M. Cecilia Sampedro et al., "Mannan from *Aloe saponaria* Inhibits Tumoral Cell Activation and Proliferation," International Immunopharmacology 4, pp. 411-418, 2004.
S. Stanilova et al., "Preliminary Investigation About the Anti-Complement Properties of Partially Separated Vipera Ammodytes Venom," Journal of Venomous Animals and Toxins, ISSN 0104-7930 Version, 1997.
Chieko Yamamoto et al, "Flavoxobin, A Serine Protease From Trimeresurus Flavoviridis (Habu Snake) Venom, Independently Cleaves Arg726-Ser727 of Human C3 and Acts as a Novel, Heterologous C3 Convertase," Immunology 107, pp. 111-117, 2002.
Schreiber Rd et al., "Raji Cell Injury and Subsequent Lysis by the Purified Cytolytic Alternative Pathway of Human Complement," National Library of Medicine and the National Intitutes of Health, www.pubmed.gov, 1980.
Suzuki I. et al., "Purification and Characterization of Two Lectins from Aloe Arborescens Mill.," National Library of Medicine and the National Institutes of Health, www.pubmed.gov, 1979.
Sundsmo JS. et al., "Activated Factor B (Bb) of the Alternative Pathway of Complement Activation Cleaves and Activates Plasminogen," National Library of Medicine and the National Institutes of Health, www.pubmed.gov, 1981.
Shimbo T. et al., "Nonspecific Activation of Complement by Leukemic Cells," National Library of Medicine and the National Institutes of Health, www.pubmed.gov, 1978.
t'Hart LA. et al., "An Anti-Complementary Polysaccharide with Immunological Adjuvant Activity from the Leaf Parenchyma Gel of Aloe Vera," National Library of Medicine and the National Institutes of Health, www.pubmed.gov, 1989.

(Continued)

*Primary Examiner*—Larry R. Helms
*Assistant Examiner*—Anne M. Gussow
(74) *Attorney, Agent, or Firm*—Bryan Cave LLP

(57) ABSTRACT

An improved more comprehensive understanding of tumors is disclosed including a precise molecular etiology leading to tumor cell growth. The disclosed molecular etiology explains the lack of control of tumor cell growth as well as the activation of a variety of phenotypic and pathological molecular mechanisms that are the natural result of the disclosed tumor etiology. A comprehensive approach to the detection and treatment of neoplasia is also disclosed.

6 Claims, No Drawings

OTHER PUBLICATIONS

Halbwachs L. et al., "Factor B of the Alternative Complement Pathway on Human Lymphocytes," National Library of Medicine and the National Institutes of Health, www.pubmed.gov, 1976.

P.J. Lachmann et al., "The Influence of C3b Inactivator (KAF) Concentration on The Ability of Serum to Support Complement Activation," Clin. Exp. Immunology 21, pp. 109-114, 1975.

Oboshi S. et al., "Rosette Formation of Human Erythrocytes on Cultured Cells of Tumour Origin and Activation of Complement by Cell Membrane," Nature vol. 248, pp. 521-522, 1974.

M.P. Dierich et al., "Detection of Proteolytic (C3-Cleaving) Activity on Mouse Mastocytoma (P 815) Cells and other Mouse Cell Lines by Formation of Cell Contract with C3-Carrying Mouse Lymphocytes," Eur. J. Immunology 9, pp. 928-932, 1979.

"Inhibition of Nephrithic Factor-Dependent C3 Convertase: Isolation of a Natural Inhibitor of C3 Conversion from the Serum of a Patient with Nephritic Factor and Nephritis", The Journal of Immunology, vol. 120, No. 5, 1978, pp. 1776-1777.

\* cited by examiner

COMPOSITIONS AND METHODS FOR TREATING CANCER

BACKGROUND

Tumors are commonly thought to result from uncontrolled cell proliferation, i.e. a cell growth which escapes the mechanisms normally regulating it. The cells in a tumor can expand exponentially. Thus, after 20 cell divisions of a single cell, nearly one million cells are formed having a volume of about 1 mm$^3$. After 30 cell divisions, about 1 billion cells are formed having a total volume of 1 cm$^3$. Tumors generally appear to grow spontaneously, anarchically, irregularly and without control by the mechanisms that regulate normal tissue development and morphogenesis. Tumor tissue is thought to be useless tissue that grows at the expense of a healthy organism. Tumor progression often leads to regional and systemic wasting effects.

Although this view stresses some aspects that are typically present in a tumor, it provides little insight into the etiology and pathogenesis of tumors, and provides little understanding of the mechanisms that give rise to the symptoms observed in cancer patients.

What is needed in the art is an understanding of tumor etiology, particularly at the molecular level. The molecular etiology will lead to an understanding of why tumor cell growth appears uncontrolled as well as to an understanding of the mechanisms of activation of the spectrum of phenotypic and pathological molecular mechanisms that are the natural physiological result of the tumor etiology. Only with a true understanding of the etiology of tumor formation at the molecular level can a more comprehensive approach to the detection and treatment of neoplasia can be implemented.

SUMMARY

A comprehensive explanation of tumor etiology is disclosed, including the precise molecular etiology leading to tumor cell growth. The disclosed molecular etiology explains the lack of control of tumor cell growth as well as the activation of a variety of phenotypic and pathological molecular mechanisms that are the natural result of tumor formation. A comprehensive approach to the detection and treatment of neoplasia is also disclosed.

A method is disclosed for treating a neoplasia in a patient in need of treatment that includes forming a mixture between a portion of a nonhuman protein having human C3 convertase activity and an inhibitor of that activity and administering a therapeutically effective amount of that mixture into a patient. The C3 convertase can be derived from plants or animals. For example, the C3 convertase activity can be derived from a snake venom such as Cobra snake venom, Habu snake venom or *Vipera ammodytes* venom. The C3 convertase activity can also be derived from plants such as *Aloe vera, Aloe arborescens, Aloe barbadensis*, or *Aloe saponaria*.

The C3 convertase inhibitor can be derived from animal serum such as mammalian serum including human serum, or the inhibitor can be derived from snake serum, such as Cobra, Habu or Viper serum, for example.

In a method, the nonhuman protein having human C3 convertase activity binds to the inhibitor.

In a method, the active agent is administered by injection which can optionally be repeated as required.

In a method, the amount of nonhuman protein having human C3 convertase activity can be in the range of about 0.1 to about 0.5 µg or more per injection.

A method for treating neoplasia in a patient in need of treatment is disclosed that includes obtaining a binding molecule that binds an inhibitor of complement and contacting the serum of the patient with the binding molecule and removing a portion of the inhibitor from the serum. Suitable complement inhibitor proteins include CF-INH, such as a *Naja Naja Kauthia* CF-INH; Factor H; Factor I; a MAC INH; SGP2; C1-INH; C567-INH and/or S. Any suitable binding molecule can be used including antibodies, or other proteins such as CVF, peptamers or aptamers and the like. The binding molecule can be immobilized to a solid support such as an apheresis or biocore support. When the binding molecule is immobilized to a solid support the step of contacting the serum of the patient can include treating the patient's serum by plasma apheresis using the solid support in the apheresis column.

A method is disclosed for detecting or treating a neoplasia that includes detecting the neoplasia by the identification of a complex between an RUHC3bL gene product and CF-INH in the serum.

Although patients having any neoplasia can benefit from the present methods, treatment of mesodermic neoplasias including liposarcomas, osteosarcomas, rabdomyosarcomas and fibrosarcomas are specifically contemplated.

A method is disclosed for treating a patient by detecting neoplasia in a patient comprising obtaining a sample of body tissue from a patient, contacting a portion of the tissue with a binding molecule that binds RUHC3bL protein and then detecting the binding of the binding molecule to the RUHC3bL protein. In a method, the binding molecule can bind RUHC3bL protein when RUHC3bL is bound to CF-INH.

A method is disclosed for detecting neoplasia that includes obtaining a sample of body tissue from a patient, contacting a portion of the tissue with a binding molecule that binds CVF protein, detecting the binding of the binding molecule to an antigen in the body tissue of the patient. Any suitable binding molecule can be used including antibodies, such as antibodies that bind CVF protein, antibodies that bind the CVF/CF-INH protein complex, antibodies that bind RUHC3bL protein, antibodies that bind RUHC3bL/CF-INH complex.

The binding molecules can be included in a kit having instructions that describe how to conduct the assay.

A kit is also disclosed for detecting cancer that includes at least one antibody that binds one or more ACP inhibitor proteins, such as CF-INH, Factor H, Factor I, a MAC INH, SGP2, C1-INH, C567-INH and S.

The kit can include at least two (2), three (3), four (4), five (5), six (6), or seven (7) antibodies or can include antibodies that specifically bind each ACP inhibitor proteins, CF-INH, Factor H, Factor I, a MAC INH, SGP2, C1-INH, C567-INH and S.

Additional features and advantages are described herein, and will be apparent from, the following Detailed Description and the figures.

DETAILED DESCRIPTION

The present disclosure is based on the discovery of a novel etiologic mechanism for the development of neoplasia and the discovery of an effective approach for its detection and treatment. Biomolecular mechanisms linking the unique causal element of neoplasia with virtually all tumor phenotypical aspects, e.g., pain, impaired function, decreased appetite, weight loss till cachexia, alterations in protein, lipid or carbohydrate metabolism, tiredness and the like, have been identified and are disclosed. Thus, it has now, surprisingly, been found that all of the various known tumor symptoms are causally linked to a unique causal mechanism.

A correlation between tumor biology, on the one hand, and chronic inflammation and pathologic wound healing has been discovered. Superficially, tumors appear to lack normal regulation or modulation and exhibit irregular shapes, anarchic growth patterns and uncontrolled growth which appears to be irreversible. Similarly, in chronic inflammation and pathological wound healing there also appears a similar lack of modulation, although this lack of modulation is reversible.

Correlations between the morphology of neoplasia and chronic inflammation and wound healing exists from three perspectives. First, cutaneous disease looks like malignant neoplasia in that lesions are asymmetric and have irregular borders, colors and dimensions. Second, cutaneous disease looks like chronic inflammation. Lastly, cutaneous disease looks like pathological wound healing.

Similarities between tumor morphology, chronic inflammation and pathological wound healing led to the hypothesis that a gene, RUHC3bL, named for Relatively Unmodulated Human C3b-like gene, is responsible for the observed similarities. It is hypothesized that a natural tumor defense system operates in conjunction with the product of the above gene to prevent neoplasia. This system is believed to exist in a liquid microenvironment that surrounds each cell. For purposes of this disclosure this microenvironment is called the microdefending unit, hereinafter the MDU. The natural tumor defense system in the MDU contains a protein system, abbreviated for purposes of this application as the ACP/ANDS (Alternative Complement Pathway/Against Neoplasm Defending System). The system includes several molecules, some of which are known for other functions, including the Alternate Complement Pathway, and some of which are new, namely the CF-INH proteins, named for Convertase Formation Inhibitor(s). In healthy cells the proteins (ACP/ANDS) in the MDU microenvironment cause self destruction of a cell through lysis when the cell becomes transformed. The lytic event is triggered by the expression of the RUHC3bL gene product which, under normal circumstances in healthy cells, activates complement resulting in cell lysis.

CF-INH molecules occur in a number of plants and animals and generally include any molecule that can bind the RUHC3bL gene product or the homologous CVF, such as from snake venom. Thus, CF-INH can be from a human or other animal including snakes where it can be found in the serum.

A natural defense against neoplasia is driven by the interaction of the RUHC3bL gene product with the MDU/ACP/ANDS, but the same RUHC3bL gene product becomes the etiologic agent of neoplasia when it interacts with an altered MDU/ACP/ANDS.

The RUHC3bL gene product is thought to be a noncatalytic enzyme subunit that, once bound to the Bb catalytic subunit of Factor B, becomes a pathological RUHC3bL/Bb C3-Convertase enzyme. RUHC3bL is thought to have a similar primary structure to the C3b subunit of C3-Convertase. The pathologic RUHC3bL gene is thought to be present in all human cells but normally is not expressed. It is believed that the RUHC3bL protein is only expressed in transformed cells and its expression is not regulated in the same manner as the C3b subunit. See Didier J. et al., "Co-expression and secretion of C3, the third component of complement and a C3-cleaving cysteine proteinase in a highly metastatic human melanoma cell line," Immunology Letters 58 (1997) 107-112. The effect that expression of the RUHC3bL gene product has on a cell is determined, in part, by the status of the MDU/ACP/ANDS system. In particular, the status of the proteins of the ACP/ANDS in the MDU determines the outcome.

The proteins of the ACP/ANDS system contain a number of inhibitors that block the action of the RUHC3bL gene product as well as downstream events in the cascade of events that this molecule triggers. In normal cells these inhibitors have a relatively low concentration such that when the RUHC3bL gene product is expressed after a transformation event, the RUHC3bL protein can eventually activate a C3 converting enzyme which then activates complement and causes cell lysis. This is thought to be a normal biological process that occurs throughout the life of an organism which guards against tumor formation.

Alteration of the concentrations of any of the inhibitors in the ACP/ANDS in the MDU can lead to a failure to lyse a neoplastic cell resulting in the development of a tumor. There are a number of inhibitors, CF-INHs, present in the ACP/ANDS system. The first in the series is a CF-INH that is thought to bind the RUHC3bL gene product to block its binding with Bb to form the active C3-converting activity. This blocks complement activation. A variety of other inhibitors are also known to be present in the ACP and these are also thought to block the downstream steps in the complement activation pathway. The inhibitors include β1H (Factor H), KAF (or C3b INHs(h) or Factor I), MAC INHs(h), SGP2, C1-INH, C567-INH and S. Should the concentration of any one of these inhibitors rise to a level sufficient to block the complement induced lytic cycle, the result is that a transformed cell will grow into a tumor.

As indicated above, CF-INH is thought to block the activity of the RUHC3bL gene product with respect to forming an active C3 convertase. Certain literature data can be interpreted in a manner that supports the conclusion that human serum contains one or more low MW inhibitors that block the formation of active C3 convertase. The inhibitors interfere with the binding of human Factor B with CVF (Cobra Venom Factor, a non-catalytic subunit of Cobra venom obtained from *Naja Naja Kauthia*), as well as C3b. In fact, by incubating CVF with human blood serum, the CVF-Bb C3-convertase does not form. (Lachmann P G and Halbwachs L, *Clin. Exp. Immunol.* "The influence of C3b inactivator (KAF) concentration on the ability of serum to support complement activation," (1975), 21, 109-114). This report can be interpreted to support the idea that one or more inhibitor(s), such as a CF-INH, binds CVF and blocks CVF-Bb formation. These inhibitor(s) are thought to bind a human molecule having a similar structure to CVF, which is identified above as the pathological RUHC3bL molecule. In addition, the existence of low MW inhibitors of complement fixation is supported by data on patients suffering from Membranoproliferative glomerulonefritis. These patients are thought to activate too much complement because of the production of an antibody that recognizes and makes the C3 Convertase C3b-Bb insensitive to inhibitors. This causes overexpression of the convertase, rendering it unmodulated, and defines the pathology of the disease. Dialysis of these patients causes a relapse of the disease. (Halbwachs L and Leibowitch J, "Inhibition of nephritic factor-dependent C3 Convertase: isolation of a natural inhibitor of C3 conversion from the serum of a patient with nephritic factor and nephritis," (1978), Dept of Nephrology and U.25, Prof. J Hamburger, Hospital Necker, Paris, France). This data may be explained on the basis of the existence of the low MW physiological CF-INH. The inhibitor inhibits C3-Convertase formation and thus it lightens the pathology. Following dialysis, serum CF-INH concentration is reduced and the disease worsens.

Other data are available that can be interpreted to support the existence of the RUHC3bL molecule. For instance, in a culture of mouse mastocytoma P815 cells, an unknown factor showing a C3 cleaving activity that is similar to a normal C3 Convertase activity was found, (Dierich M P et al., "Detection of proteolytic (C3-cleaving) activity on mouse mastocytoma (P815) cells and other mouse cell lines by formation of cell contact with C3-carrying mouse lymphocytes" *Eur. J. Immunol.,* 1979, 9(12), 928-932). This data can be explained by assuming that Factor B is synthesized by B lymphocytes under the action of RUHC3bL, such action being similar to that of CVF on lymphocytes (Halbwachs L and Lachmann P J, "Factor B of the alternative complement pathway on human lymphocytes," *Scand. J. Immunol.,* 1976, 5(6-7): 697-704). C3 Converatse activity is consistent with the findings of others. (H. Okada, T. Baba, "Rosette formation of human erythrocytes on cultured cells of tumor origin and activation of complement by cell membrane," *Nature,* 1974, 248, 521-522.) This observation can be explained by the binding of RUHC3bL with Factor B to create a C3 convertase which allows erythrocyte binding on the cell. The same holds true for the findings of Shimbo et al. (Shimbo T et al, "Nonspecific activation of complement by leukemic cells," *Int. J. Cancer,* 1978, 22(4), 422-425); Okada N and Okada H, "Activation of complement by spontaneous leukemic cells of AKR mice," J. Int. Cancer, 1978, 15: 282-7) and Schreiber R D et al., "Raji cell injury and subsequent lysis by the purified cytolytic alternative pathway of human complement," *Clin. Immunol. Immunopathol.,"* 1980, 15(3): 384-396). When the serum of patients recovering from Hypo Complementemic Glomerulonephritis (HCG) are treated by dialysis to remove molecules having a molecular weight of less than about 2,000 they relapse. This is can be interpreted as occurring by a mechanism that involves CF-INH. While these studies can be interpreted in a manner that supports the present disclosure concerning the etiology of cancer, they have not previously been implicated in the etiology of cancer or as defining targets for its cure.

When a cell becomes transformed, the RUHC3bL gene is expressed and its protein product is translocated into the MDU where it encounters the molecules of the ACP/ANDS. The ACP/ANDS consists of a number of molecules of the Alternative Complement Pathway, including Convertase formation inhibitors (CF-INHs), among other proteins. The proteins are present in very low amounts in the MDU and in higher amounts in the serum. The RUHC3bL gene product binds CF-INH more tightly than Factor B in the MDU or serum. The complex signals that the cell is transformed.

The formation of a complex between the RUHC3bL gene product and the inhibitor protein, CF-INH, is thought to be the first step occurring after cell transformation. CF-INH blocks the lytic cascade, while reducing the free concentration CF-INH inhibitor in the MDU. Although serum concentrations of CF-INH proteins are believed to be about 30-fold higher than in the MDU, the loss of these proteins in the MDU leads to a temporary reduction in the CF-INH inhibitor concentration. This reduction is thought to be corrected only after the CF-INH proteins have had a chance to diffuse into MDU from the serum. When the CF-INH inhibitor concentration falls, a portion of the RUHC3bL gene product is not bound by CF-INH inhibitor and remains free to bind Bb to form an active C3-Convertase which in turn activates complement through the ACP pathway. This eventually leads to the lysis of the transformed cell to prevent the formation of a tumor.

The ACP/ANDS proteins are also components of a system of natural non-adaptive immunity. The ACP system includes the proteins C3, B D, P, which in the presence of Mg++ are all known to be responsible for the activation and amplification of the cascade that leads to cell lysis. A number of membrane attachment complex proteins are also thought to be involved in the ACP/ANDS system. These include C5, C6, C7, C8 and C9. Additional inhibitors (see above) are also thought to be involved in the following steps of ACP activation. These proteins are all present both in the serum and in the MDU layer surrounding each cell in the body although the serum generally contains about 30-fold higher concentrations. The serum serves as a pool of these proteins for their continuous replenishment around the cell MDU.

If the concentration of these proteins in the MDU is out of a physiological range, the ACP/ANDS system cannot function properly. When the concentration of CF-INH and/or other inhibitors is high in the MDU system, the process of cell lysis is not triggered properly, transformed cells are not lysed and can grow into a tumor. In addition, because the transformed cell is not removed from the organism, it continues to produce the RUHC3bL gene product. Eventually the RUHC3bL gene product saturates the MDU of the cell, forms complexes with the CF-INH proteins and the complexed RUHC3bL gene product diffuses out of the MDU and away from the cell into the surrounding areas and eventually into the serum. Due to the short half life of CF-INH, the RUHC3bL gene product can become inhibitor free for short periods of time. When this occurs, the RUHC3bL-Bb Convertase activity can be found outside of the cell where the variety of different symptoms associated with cancer can begin to appear. The region where this RUHC3bL-Bb Convertase activity is produced becomes hypocomplementemic as evidenced by the formation of a hypocomplementemic halo.

The RUHC3bL activity may also help to explain many traits of tumors, for example with respect to Plasminogen Activator (PA) activity. It is thought that the C3b/Bb complex normally involved in complement activation has a certain level of PA activity, even if its structure is known to be quite different from that of Urokinase or of tissue-type PA (Sundsmo J. S. and Wood L. M. "Complement Factor B: Plasminogen activator," *J. Immunol.* 1981, 127(3) 877-880). The RUHC3bL/Bb complex is thought to have a similar enzymatic activity profile, having C3 Convertase activity as well as PA activity. The difference with the RUHC3bL/Bb activity is that it is relatively unmodulated consistent with its unmodulated expression. This helps to explain a significant phenotypical aspect of tumors, namely unmodulated plasminogen activator activity.

In this scenario macrophages and other immune cells are thought to be attracted to the vicinity of the tumor cell where they are thought to synthesize all the fluid phase ACP inhibitors leading to an increase in their local concentrations. Simultaneously, the transformed cell, in response to the presence of activated ACP over expresses surface phase inhibitors known as membrane Complement Regulatory Proteins as a protection mechanism against lysis. Moreover, macrophages will not attach to cell membranes through C3b, since C3b is consumed by the active RUHC3bL/Bb.

The present disclosure covers methods for detecting tumor formation by detecting these proteins, especially by detecting the presence of the complex between the RUHC3bL gene product and the CF-INH. Detection of this complex provides a diagnosis of neoplasia. The identification of any amount of this complex in the serum provides an indication that a transformation event has taken place in a cell and the concentration of this complex in the serum provides an indication of how far the disease has progressed and how much tumor mass may exist.

Methods for preparing antibodies to RUHC3bL, CF-INH and the complex between these two molecules are disclosed below. These antibodies can be used in a variety of known immunological assays to determine the concentrations of their respective antigens in the serum of patients. For example, elisa, ouchterlony and Mancini, radial immunodiffusion methods are well known in the art and can be used. Alternatively, well known affinity chromatography techniques can also be used to determine the amount of antigen present in a known quantity of serum or other cellular material. In addition to the antibodies that bind the target molecules, such columns can also be prepared using Factor B or CF-INH from man or *Naja Naja Kauthia*. A variety of methods for purifying these proteins are known in the art and can be used.

Diagnostic methods can be used to ascertain the concentrations of the inhibitor proteins and indeed the concentrations of each of the individual components of the ACP/ANDS system either in the serum or in tissue samples. This information can be used directly to remediate disease, to monitor the status of the disease, update the prognosis of the disease or to obtain an early diagnosis for the disease. For example, when concentrations of particular inhibitors, such as CF-INH, are too high, an antibody or other binding molecule that selectively binds the inhibitor can be used to filter the serum and remove the inhibitor, thereby lowering its concentration in the serum and therefore also in the MDU of each cell in the body, especially including the MDU of transformed cells. Many methods are known for reducing the concentrations of molecules found in the serum and can be used. In one method, a protein or protein sequence having a similar primary structure to the inhibitor but with sufficient variation to be immunogenic can be used in a vaccine to initiate an immune response that will reduce the concentration of that protein in an animal. Such proteins can be found in organisms other than the target organism. For example, in an embodiment a mixture of *Naja* serum and CVF can be used. In such a mixture the CVF can become fragmented and the fragments can bind *Naja* CF-INH. Such a mixture and/or the resulting complexes, once injected in man, stimulate the production of antibodies that, due to *Naja* CF-INH epitopes present in the complexes, are also thought to bind human CF-INH. More generally, such antigens can be used to generate an immune response and antibodies that will react with any of the various inhibitor proteins from the MDU in a patient thereby reducing the level of the free inhibitor. Alternatively, antibodies or other binding molecules that bind the inhibitor can be injected directly into the serum of a patient or can be used to filter the serum, such as by affinity column plasma apheresis or other systems using the affinity chromatography method. Such devices are available commercially by companies, such as Biacore. Plasma apheresis is preferred, especially in those patients having depressed immune systems.

When the ACP/ANDS/MDU system is restored to a normal healthy situation, it is thought that tumor cells will be eliminated using normal biological processes. A properly functioning system has the capacity to resolve the neoplasia without the use of toxic agents and results in the restoration of the organism to a normal regulated state which results in the clearance of neoplastic cells from the organism through natural processes.

Many types of binding molecules are known and can be used for reducing inhibitor concentrations. Suitable binding molecules include antibodies, antibody mimetics, aptamers or protamers that specifically bind individual inhibitors, such as CF-INH inhibitors. Antibodies, antibody mimetics, aptamers or protamers that bind inhibitors can be generated by known methods and such binding molecules can be immobilized and used in methods such as apheresis to remove or reduce inhibitor concentrations. For example, an antibody has been generated in response to injection of a mixture containing CVF and CF-INH obtained from *Naja Naja Kauthia*. This complex is thought to resemble the complex between the human RUHC3bL gene product and CF-INH. Such an antibody may crossreact and can be used in the determination of serum levels of human RUHC3bL/CF-INH and in the treatment of neoplasia.

In one method the therapeutic approach involves forming a mixture between CVF and a Cobra serum composition and injecting the mixture into a patient afflicted with cancer. However, the method is not intended to be limited to the use of Cobra CVF. Any protein having human C3 convertase activity, of which many are known could be used. For example, such human C3 convertase proteins are known in a variety of plants and animals. In snakes such proteins are known in venomous snakes such as Cobra and Habu snakes. With respect to snake venom, the venom from the snakes *Naja Naja Kauthia*, *Trimeresurus flavoviridis* snakes and *Vipera ammodytes* can be used as suitable sources for such proteins. With respect to plants, suitable plants include *Aloe vera* (t'Hart L A, van den Berg A J, Kuis L, van Dijk H, Labadie R P., "An anti-complementary polysaccharide with immunological adjuvant activity from the leaf parenchyma gel of *Aloe vera*," *Planta Med.* 1989 December; 55(6):509-12), *Aloe arborescens* (Mill (Suzuki I, Saito H, Inoue S, Migita S, Takahashi T., "Purification and characterization of two lectins from *Aloe arborescens*" Mill., *J. Biochem.* (Tokyo). 1979 January 85(1):163-71.), *Aloe barbadensis* (Kardosova A, Machova E., "Antioxidant activity of medicinal plant polysaccharides.," *Fitoterapia* 2006 May 24;), *Aloe saponaria* (M. Cecilia Sampedro, Rodolfo L. Artola, Mariano Murature, Domingo Murature, Yanina Ditamo, German A. Roth and Silvia Kivatinitz, Mannan from *Aloe saponaria* inhibits tumoral cell activation and proliferation, *International Immunopharmacology*, 4, Issue 3, March 2004, Pages 411-418).

By inoculating patients with heterospecific complexes of CVF fragments and *Naja* CF-INH inhibitors, the antigens are sufficiently different enough from their human homologous counterparts to induce antibody production. Yet, they are similar enough so that the antibodies produced will crossreact with the corresponding human inhibitor. Antibodies produced in response to such injections have been successful in permanently remediating cancer in a number of cases. It is believed this occurs by removing excess inhibitors from the circulation thereby making the ACP/ANDS system in the MDU effective again. Although suitable heterospecific inhibitors were found in the serum of *Naja Naja Kauthia*, they are also likely to exist in a variety of other organisms. Such inhibitors can be identified using protein sequence comparison programs to identify protein sequences having homology to the *Naja* CVF and CF-INH proteins.

Thus, other molecules than CVF or its fragments could be used, for example molecules from the venom of different snake species (cf. Yamamoto C et al., "Flavoxobin, a serine protease from *Trimeresurus flavoviridis* (habu snake) venom, independently cleaves Arg726-Ser727 of human C3 and acts as a novel, heterologous C3 convertase," *Immunology* 2002 September; 107(1):111-7). In addition, heterologous molecules functionally similar to CVF in its ability to bind the CF-INH, complexed with either human or non-human CF-INH, could be inoculated to elicit antibodies against CF-INH epitopes, thus likely crossreacting with human CF-INH. Such heterologous molecules could be obtained from different living species (not necessarily venomous snakes, but also non-venomous snakes, as well as other living beings) or even by synthesis. For sake of simplicity, in the present disclosure only the CVF molecule or its fragments have been referred to, but implicitly all the different molecules functionally similar to CVF in binding the C3 Convertase inhibitor(s) CF-INH are to be considered as interchangeable with CVF.

Protein sequences having about 40 or about 50% or more homology to the *Naja* proteins (CF-INH and CVF) can be used. Similarly, sequences having higher levels of homology can also be used, for example proteins having about 60% or more, about 70% or more, about 80% or more about 90% or more, about 95% or more can be used. Similarly, the sequences of the *Naja* proteins can be subjected to mutations to change one, two, three, four or more amino acids or can be subjected to mutagenesis reactions which change about 1, 2, 3, 4, 5, 6, 7, 8, 9 or about 10% of their amino acids and the proteins generated can be used to generate antibodies, using standard methods, that can be used to diagnose and remediate cancer and provide antibodies for the diagnosis and remediation of cancer.

All patients treated by the *Naja* serum mixtures showed favorable clinical signs, even if the disease did not completely disappear. Favorable clinical signs include an improvement of life expectancy and quality of life. In every case, the treatment effects were localized to the sites of neoplastic lesions.

The treatments can be carried out by mixing 20 μL of filtrate of *Naja Naja Kauthia* serum from about 10 to about 50 kD cut-off filters with 20 μL of commercially available CVF (at about 1 μg/μL concentration) and incubating the mixture at about 26° C. for about 2 h. The mixture can be diluted into about 4 mL $H_2O$ or other buffers, such as PBS. Next about 1.8 mL of alhydrogel 3% can be added to adsorb the antigens for controlled release. Approximately, 12 doses of 500 μL can be obtained from this bulk. Approximately 130 μL of 400 mM tyrosine can also be added, together with sodium merthiolate (Thimerasol) to reach a concentration of about 10 μM. The mixture can be further sterilized by filtration (Millex 0.25 or 0.45) and stored at 4° C. The doses can be injected subcutaneously every 18-20 days. Such mixtures can be characterized by electrophoresis and other standard methods as are known in the art prior to use.

Patient diet is preferably high in potatoes, apples, pumpkins and low in oranges, lemons, tomatoes. Moderate amounts of sodium bicarbonate in drinking water are also suggested. This is thought to increase the activity of the ACP/ANDS.

The above methods can be used with success in the treatment of any patient having cancer. It has been observed that patients presenting mesodermic neoplasias including liposarcomas, osteosarcomas, rabdomyosarcomas and fibrosarcomas are very responsive to treatment and are, in general, rapidly and completely healed. However, all types of cancer can be treated, since virtually all patients given this treatment demonstrated a positive response to treatment, particularly soon after treatment. In some cases the response diminished after a period of time. This is thought to be caused by the involvement of other ACP inhibitors in the MDU. Similar treatments that target these inhibitors are also envisioned.

Serum from patients that are cured by the above treatment can be isolated and antibodies prepared by affinity purification through columns containing an immobilized protein such as CVF, CF-INH, or the CVF/CF-INH complex in order to obtain antibodies against RUHC3bL/CF-INH. Such columns can be used directly or the antibodies can be isolated and immobilized on a solid support and serum from untreated patients can then be filtered. Using this strategy patients can be treated and, at the same time, the disclosed etiologic cancer agents can be isolated and characterized. Once the binding sites on the columns approach saturation the bound sites can be regenerated by removing the antigens using methods well known in the art. Such columns can be used to isolate the human agent that corresponds to CF-INH, CVF (RUHC3bL) and the complexes between these proteins. Such columns can also be used with extracts from any suitable source that contains CF-INH, CVF (RUHC3bL) proteins. Patients are not required. For example, cell cultures from surgical biopsies of cancer patients could be used, preferably in serum free medium or other cell cultures containing cancer cells could be used.

Each of the following inhibitors are also thought to be involved in the ACP/ANDS system including β1H (Factor H), KAF (or C3b INHs(h) or Factor I), MAC INHs(h), SGP2, C1-INH, C567-INH and S. Binding molecules such as antibodies, antibody mimetics, aptamers and protomers can also be generated against these known proteins using standard methods and used in the diagnosis and treatment of cancer using the previously described methods for CF-INH. Thus, an antibody can be generated against Factor H or against a mixture that contains Factor H and its target protein and then used to determine the concentration of Factor H in a cancer patient. If the Factor H level is elevated, the patient can be treated by filtering the patient's blood using apheresis with the antibody or other binding molecule immobilized to an apheresis column for Factor H until the concentration returns to a normal physiological concentration. The same process can be carried out with each of the inhibitors listed above and any inhibitor involved in the ACP/ANDS system. Preferably, such tests will be conducted with two, three, or four or more of the inhibitors and more preferably with each of the known inhibitors such that a broad spectrum of inhibitor concentrations can be determined in a cancer patient and the patient can then be treated to restore the inhibitor concentrations found to be abnormal to their normal physiologic ranges.

Other antigens can also be used to accomplish the same results. For example, a plasmin-α2-antiplasmin complex (PL/AP) could also be used in place of the CF-INH/CVF mixture.

The identification of the RUHC3bL gene product as an etiological agent of neoplasia also provides an explanation for other symptoms of neoplasia including unregulated plasmin formation leading to hyper-fibrinolysis, complement activation, quinines and quinidine activation, renin-angiotensin activation, which may all arise indirectly through RUHC3bL gene expression.

As tumors develop it is often the case that cell proliferation is higher than the angiogenesis rate. As a consequence, the MDU surrounding a portion of the tumor cells may not be replenished by the blood serum. In such cells the inhibitor levels may actually decrease and become normal with the result that the normal process of ACP mediated lysis and necrosis occurs. In areas that are adequately vascularized the transformed cells continue to divide.

The RUHC3bL gene product has a direct effect on increasing the level of plasmin because it has plasminogen activating activity. After a transformation event the increased levels of RUHC3bL gene product directly results in an relatively unmodulated increase in plasmin, increased fibrinolysis and ultimately in hyper-fibrinolysis and germ independent inflammation.

Expression of the RUHC3bL gene product may also explain the useless (because of the hypocomplementemic halo around the transformed cells) macrophages attraction. The RUHC3bL gene product may also determine the alterations of carbohydrate, protein and lipid metabolism which are frequently observed in cancer patients. For example, it is known that in some cases neoplastic tissue can utilize up to $\frac{1}{10}^{th}$ its mass in glucose per day, yet many patients are also hypoglycemic which leads to the conversion of protein into glucose in affected patients. This may occur because the RUHC3bL gene product may locally and unmodulately activate proinsulin transformation into insulin. Moreover, the plasminogen activator activity can also lead to unregulated growth factor activation of other growth factors and thus activating tumor uncontrolled growth.

Example 1

This example provides a case study of a patient having an advanced tumor known as a spinocellular carcinoma. The tumor could be observed in a static condition, at the time of the first exam, and in a dynamic condition, during the successive treatment. It was a spino-cellular cancer devastating the patient's appearance. It presented the classical traits of cutaneous lesions, consisting of asymmetry (overall irregularity), irregular borders, various end and irregular colors, various and irregular dimensions. At the time of the first examination the patient's prognosis was poor and the life expectancy was short. The tumor clearly displayed all of the classical traits of such cancers, namely, the etiologic and pathogenetic mystery of the lack of modulation in every aspect (the tumor cell is altered, spontaneously developing, uncontrolled, anarchic, purposeless, irregular in all its traits).

The patient experienced tremendous pain because of encephalic nerve involvement and demonstrated extreme hyper-fibrinolysis with a continuous drip sero-hematic liquid which rapidly gave rise, by the effect of bacterial involvement, to an unpleasant smell. The volume of these secretions was about 28 mL/12 h. Alimentation was extremely difficult, the general state was severe, sub cachectic with alternating and modest fever leading to a poor short term prognosis. The hematic vascular dynamics were irregular and uncontrolled. Redness in the area of the neoplasia was accompanied by regional cutaneous hyperthermy. Lymphatic vascular dynamics were also irregular. Pale zones were associated with a tactile objective feeling of hypothermia.

The patient was treated by injections of a mixture of serum proteins from the organism *Naja Naja Kauthia*. The patient developed antibodies to these proteins which cross reacted with his own serum proteins resulting in the clearance of his excess ACP inhibitors and curing the cancer by making the MDU/ACP/ANDS effective. The treatment reversed hyperfibrinolysis to the extent that the cancerous lesion dried up. This hyperfibrinolysis removal led the inventor to point his attention on C3b function as fibrinogen activator and to the hypothesis of the existence of the RUHC3bL gene product as the first etiologic agent not only of the hyperfibrinolysis, but of the other aspects of tumors too. This response was followed by addition research in which the *Naja* serum proteins were purified from the raw materials initially available.

Within 60 days after immunogen treatment the fibrinolysis was markedly reduced, clotting appeared more normal and the borders of neoplastic wound healing appeared more normal. These effects increased further at 90 days after treatment.

The Spino-Cellular Cancer receded with dried healing and epithelium formation along the borders. Pain, regional paresthesias, macro- and micro-circulatory alterations and local hyperthermia totally disappeared. Analgesic consumption fell from 8 to just one pill before sleeping. The Spino-Cellular Cancer patient returned to live a livable life for 6 more years and eventually passed away from other causes.

In conclusion, the different aspects of anarchist, nonsense, irregular, uncontrolled behavior of a tumor may all be derived from the sole RUHC3bL gene product, which is at the apex of a pyramid of all different tumor characters.

Example 2

This example shows that the result obtained in Example 1 is reproducible and can be applied to the treatment of other tumor cells. A patient suffering from a hyperfibrinolytic unmodulated basal cell carcinoma of the back skin was treated by utilizing the same substances as in Example 1, but more purified, and a similar response was observed. The Basal Cell carcinoma receded too, with dried healing and epithelium formation along the borders. The patient was alive more than 38 years after treatment and was in good health.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A method for treating a skin cancer in a patient in need of such treatment, the method comprising forming a mixture of Cobra venom factor (CVF) and serum of *Naja Naja Kauthia*, and administering said mixture into a patient.

2. The method of claim 1, wherein the administration is by injection.

3. The method of claim 1, wherein the administration is by injections that are repeated.

4. The method of claim 1, wherein the amount of the mixture of Cobra venom factor (CVF) and serum of *Naja Naja Kauthia* administered to the patient is in the range of about 0.1 to 0.5 micrograms per injection.

5. The method of claim 1, wherein the skin cancer is a spinocellular carcinoma.

6. The method of claim 1, wherein the skin cancer is a basal cell carcinoma.

* * * * *